United States Patent [19]
Glazenburg et al.

[11] Patent Number: 5,580,564
[45] Date of Patent: Dec. 3, 1996

[54] METHOD FOR MODIFYING THE CELL, TISSUE OR HOST TROPISM OF MICROORGANISMS; RECOMBINANT MICROORGANISMS OBTAINED IN THIS WAY AND USE THEREOF IN MEDICINE AND VETERINARY MEDICINE

[75] Inventors: Koenraad L. Glazenburg; Robertus J. M. Moormann, both of Dronten, Netherlands

[73] Assignee: Akzo Nobel N.V., Arnhem, Netherlands

[21] Appl. No.: 363,202

[22] Filed: Dec. 22, 1994

Related U.S. Application Data

[63] Continuation of Ser. No. 977,448, Apr. 15, 1994, abandoned.

[30] Foreign Application Priority Data

Aug. 15, 1990 [NL] Netherlands ............................ 9001828

[51] Int. Cl.$^6$ ............................ C12N 15/00; C12N 7/04; A61K 39/12; C07H 21/04
[52] U.S. Cl. .................. 424/229.1; 424/815; 435/172.1; 435/172.3; 435/236; 536/23.1; 536/24.1
[58] Field of Search ............................ 424/93.2, 224.1, 424/229.1; 435/236, 172.3

[56] References Cited

U.S. PATENT DOCUMENTS

Re. 33,772 12/1991 Berns et al. .
5,047,237 9/1991 Cochran et al. ........................ 424/89

FOREIGN PATENT DOCUMENTS 8505629 12/1985 WIPO .
9006367 6/1990 WIPO .

OTHER PUBLICATIONS

A. Gielkens et al., "Genome Differences among Field Isolates and Vaccine Strains of Pseudorabies Virus," *J. gen. Virol*, 66:69–82, (1985). GB only pp. 69 & 70 considered since only pp. 69 & 70 were submitted.
*Virus Infections of Vertebrates 2*, Elsevier Science Publishers B.V., p. 39, "Pseudorabies Virus (Aujeszky's Disease)".
J. T. van Oirschot et al., "Some Characteristics of four attenuated vaccine virus strains and a virulent strain of Aujesky's disease virus," *The Veterinary Quarterly*, vol. 6, No. 4, pp. 225–229, 1984.
*Veterinary Virology*, Academic Press, Inc., pp. 353–357, 1987.

*Primary Examiner*—Suzanne E. Ziska
*Attorney, Agent, or Firm*—Mary E. Gormley

[57] ABSTRACT

The invention relates to a microorganism having a modified cell, tissue or host tropism whereby at least one gene of the microorganism, preferably an essential gene, is brought under the control of a nucleotide sequence specific for the cell, the tissue or the host. The specific nucleotide sequence can be a promoter sequence and/or enhancer sequence, which can be inducible. The invention is also directed at the use of such a recombinant microorganism for the provision of protection against the corresponding natural microorganism.

3 Claims, 1 Drawing Sheet

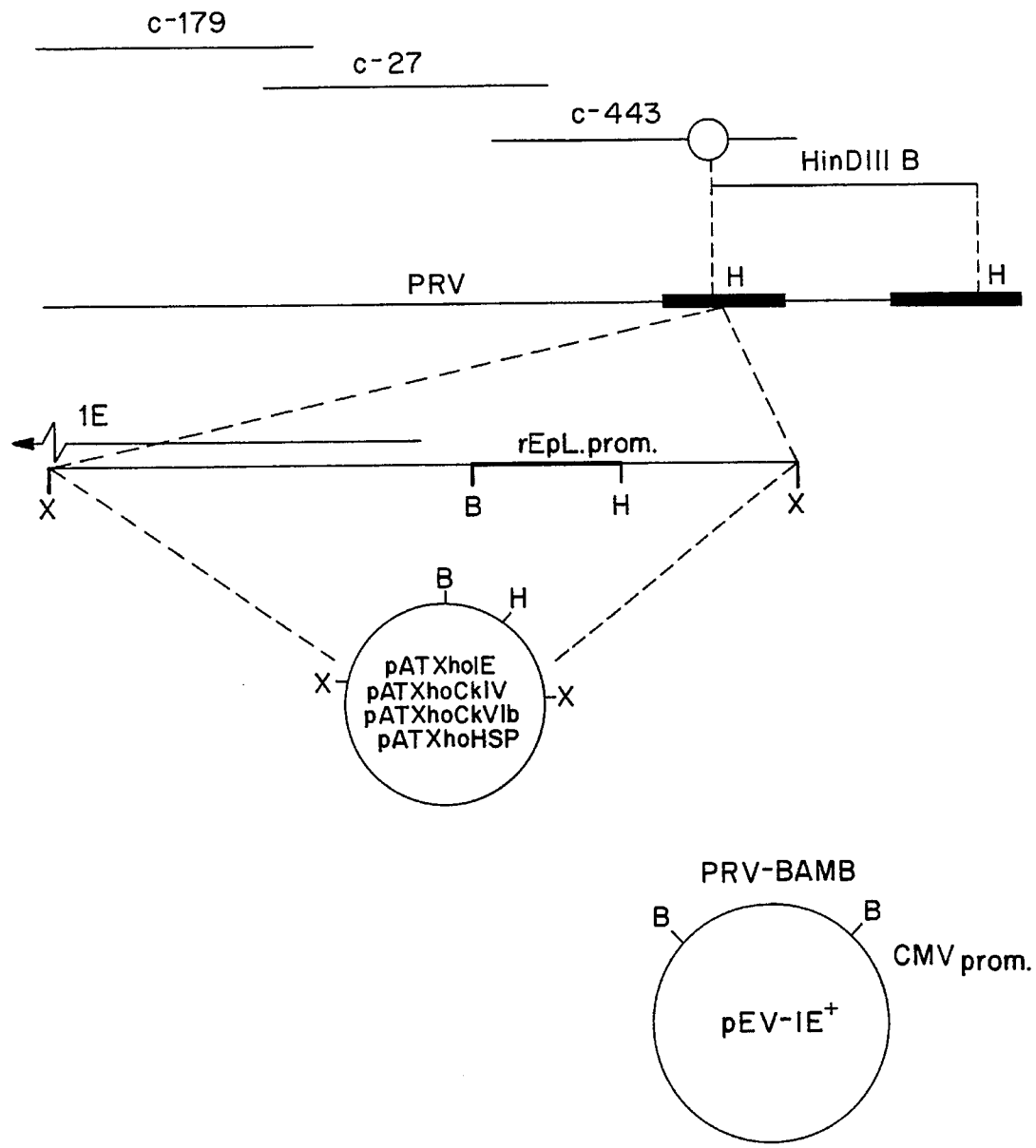

METHOD FOR MODIFYING THE CELL, TISSUE OR HOST TROPISM OF MICROORGANISMS; RECOMBINANT MICROORGANISMS OBTAINED IN THIS WAY AND USE THEREOF IN MEDICINE AND VETERINARY MEDICINE

This is a continuation of application Ser. No. 07/977,448 filed Apr. 15, 1994, now abandoned.

The invention relates to a method for modifying the cell, tissue or host tropism of a microorganism.

In many cases of infections by microorganisms the location at which the microorganism enters the organism is not the same as that where the pathogenic characteristics or the microorganism are expressed. Thus, an infection can also proceed via a variety of tissues and cell types. The herpesvirus pseudorabies (PRV) is an example of a microorganism which shows little selectivity with regard to its host cells. This virus does not only have a broad host spectrum (species-specificity) but is also able to replicate in virtually any cell line maintained in vitro (cell/tissue specificity).

The provision of protection against such a microorganism of low specificity presents problems. In the case of vaccination with a live vaccine, the virus does not only give rise to an immune reaction in the intended cells, tissues or hosts but is also able to be expressed in other cells, tissues or hosts where the microorganism can have an unacceptable harmful effect. It is possible for vaccine viruses to be transferred from their host to other hosts by means of saliva, faeces, milk and the like. These other hosts, for example young animals or animals of a different breed, which are more sensitive to the vaccine virus, become infected, so that they become ill and/or die.

The abovementioned problem can be prevented by using dead virus or parts of a virus, instead of live virus, as the immunological constituent of a vaccine. However, this method of vaccination leads less frequently to protection than vaccination with live virus and is therefore not always effective.

Another solution to the problem is given by, for example, using a weakened or otherwise modified strain as vaccine strain when providing protection against a virus. Thus, European Patent Application EP-A-141.458 discloses a deletion mutant of pseudorabies virus which, as a consequence of the mutation, is less infectious but has good immuno-logical characteristics. International Patent Application WO/8704463 (EP-A-256.092) discloses a recombinant herpesvirus which contains a foreign DNA sequence which is expressed, so that serological differentiation is possible. EP-A-119.025 discloses a mutated bovine herpesvirus which does not produce thymidine kinase and is temperature-resistant: vaccination with these mutants leads only to efficient replication in non-neural cells.

It is known that viruses do not always have pathological consequences in all infected tissues. In the case of viruses mutated in accordance with these publications, however, the specificity fop a specific cell, a specific tissue or a specific host is not increased or is inadequately increased, so that no or insufficient differentiation can be made between the desired, for example immunogenic, action of the virus and the undesired, for example cytocidal, action of the virus.

The aim of the invention is to provide a microorganism having a modified cell, tissue or host tropism, in particular a limited tropism, that is to say an increased specificity for one cell, tissue or host, in such a way that the desired action of the microorganism can be directed at specific sites without undesired effects of the microorganism being expressed to an unacceptable degree at other sites.

The aim of the invention is achieved in that at least one gene in the microorganism is brought under the control of a nucleotide sequence specific for the intended cell, the intended tissue or the intended host.

The gene can be a gene essential for the organism, optionally in combination with a gene which codes for an active substance in order to achieve the desired effect of the microorganism. Such a substance can be a protein of which there is a shortage or a medicine.

The term "an essential gene" can, for example, comprise a gene which plays an important role in the reproduction of the microorganism. In the case of a virus, for example, it can be a gene which codes for essential membrane proteins, the capsid protein or a protein which is involved in replication.

Numerous essential genes of viruses have been described. Below a number are given:

The gH-gene of pseudorabies virus (PRV) and infectious bovine rhinotracheitis virus (IBRV) is described in the International Patent Application WO/10965 of the Upjohn Company. The gII-gene of PRV is described in J. of Virology 65, 1991, p. 621–631 and in Proceedings of the 16th Int. Herpes virus Workshop Pacific Grove USA, 1991, p. 243 the gp50-gene of PRV is described.

A number of genes are described of the HSV-virus, such as the Ul 42-gene in J. of Virology 65, 1991, p. 700–710, the Vmw 175-gene in J. Gen. Vir. 71, 1990, (4) p. 851–861, the ICP-27-gene in J. of Virology 63, 1989, p. 18–27 and the Ul 8-gene in J. of Virology 63, 1989, p. 591–599.

In J. of Virology 63, 1989, p. 101–110 the nuclear antigene EBNA-1 of EBV is described.

In J. of Virology 49, 1984, p. 190–199 the major immediate early gene of HCMV is described.

The B1-gene of vaccinia is described in J. Biol. Chem. 264, 1989, p. 21458–21461 and in PNAS 87, 1990, p. 6191–6195 the E2A-gene of Adenovirus type 5 is described.

In the case of a bacterium, it can be a gene that codes for a protein which, for example, is involved in the metabolism of essential amino acids or of adhesion factors or is involved in the replication.

The *Escherichia coli* Sec Y-gene is described in J. Bioenerg-Biomembr. 22, 1990, p. 5299–5306 and the Escherichia coli Nus G-gene is described in J. Bacteriol. 172, 1990, p. 1621–1627.

The off II of the pai-gene of Bacillus subtilis is described in J. Bacteriol. 172, 1990, p. 1783–1790.

Essential genes are also known for other organisms than viruses and bacteria such as for yeast the gene that codes for the ARS-binding protein ABF-1 (Gene Dev. 3, 1989, p. 1926–39). The gene that codes for phytoene dehydrogenase (PD) of the carotenoid biosynthesis route of all microorganisms and plants containing these colour pigments (Gene 91, 1990, p. 113–117).

A specific nucleotide sequence is understood to be a nucleotide sequence (DNA or RNA) which only has a regulating action in one or more specific cell types, tissues or hosts. A number of literature references are given below in which examples of specific regulating sequences are described:

In Cell 56, 1989, p. 979–986, Greaves, D. et al. describe that human CD2 3'-flanking sequences give rise to a high degree of T-cell specific gene expression in transgenic mice, which is independent of the location.

J. H. Mar and C. P. Ordahl describe a strong muscle-specific promoter element derived from the cardiac troponine T (cTNT) gene in Mol-Cell-Biol. 10, 1990.

In the International Patent Application of Dana-Farber Cancer Institute (WO 85/05629) modified or non-modified sequences of the long terminal repeats of retro viruses, in particular the U3-regions of Akv and S1.3-3 which are respectively induced in T-cells and fibroblasts are described.

In J. of Virol 64, 1990, p. 4792–4798 the HPV-18 E-6 promoter is described, which is tissue specific in differentiating keratinocytes.

In Nature 329, 1987, p. 174–178, Wirth, T. et el describe that an oligonucleotide octamer which is located upstream of a TATA sequence is sufficient for promoter action which is specific for lymphs.

Furthermore, in Cell 60, 1990, p. 461–472, Okamoto, K., et al. report that a new octamer binding transcription factor is expressed differentially in embryogenic mice.

Moreover, in Cell 56, 1989, p. 969–977, Blom van Assendelft, G. et al. report that the beta-globulin dominant controlling region activates homologous and heterologous promoters in a tissue-specific manner.

The tissue specificity of the expression of liver genes is described by Kugler, W. et el. in NAR 16, 1988, p. 3165–3174.

In addition, in NAR 17, 1989, p. 939–953, Rijffel, G. et al. describe that the HP1 promoter elements and the TATA sequence are required and are sufficient to give a liver-specific promoter.

A rat tyrosine aminotransferase TAT-gene promoter is described in Mol-Cell-Biol 10, 1990, p. 3334–3342 which is activated in the liver.

In Mol-Biol-Med 7, 1990, p. 173–185 an albumine gene promoter is described which is activated in hepatoma cells. Additionally in Dev. Biol 139, 1990, p. 121–133 a Drosophila glue gene (Sgs 3) is described with a promoter which is activated in the salivary gland.

In EMB0 J 8, 1989, p. 1559–1565 a Drosophila-beta-2-tubuline-gene is described which is activated in the testis.

In Cell 56, 1989, p. 969–977 the dominant control region DCR of the human beta-globuline-gene is described which specifically induces in red blood cells.

In Mol-Cell-Biol 10, 1990, p. 2738–2748 a human carcinoembryonic antigene gene promoter is described which can be activated in intestinal tumor tissue.

Numerous further examples of nucleotide sequences of this type are to be found which can possibly be used for the purpose of the present invention.

Thus, the invention provides a microorganism which can only exert a specific desired function, such as the initiation of a defence mechanism or the administration of a medicine or another active substance, in a specific environment.

The microorganism of which the tropism can be modified in this way can be a virus, but also a bacterium, a mould or a parasite. The tropism of a microorganism can also be modified, for example, in that a gene is placed under the control of an inducible regulating nucleotide sequence. An inducible regulating nucleotide sequence of this type is, for example, a regulating nucleotide sequence which only comes into action under the influence of specific physical or chemical stimulation, such as, for example, hormones, pharmaceuticals, metal ions and the like. Inducible substances of this type can be specific for a cell, a tissue or host, as a result of which the expression of the gene and also the intended action of the microorganism are likewise specific for a cell, tissue or host. In Cell 56, 1989, p. 335–344, Beato, M. describes, for example, gene regulation by means of steroid hormones. In Science 236, 1987, p. 1237–1245, Maniatis, T. et al. report the regulation of inducible and tissue-specific gene expression. The abovementioned applications are particularly suitable for bacteria.

Furthermore in Prog-Clin-Biol-Res. 344, 1990, p. 123–138 a Rat Glutathion transferase P-gene promoter is described, which is induced with TPA (tumor inducer hepatocarcinogesis); additionally in Mol. Microbiol. 3, 1989, p. 1425–1432 the Streptomyces cacaoi, beta-lactamase gene promoter is described as being induced by a beta-lactam and in EMBO J. 8, 1989, p. 1641–1648 it is reported that Phenylanaline ammonia-lyase (PAL) of Peterselium crispum is induced by UV-light.

The specific nucleotide sequence is advantageously a specific promoter/enhancer. In this case, the promoter/enhancer of at least one gene is replaced by a promoter/enhancer which is specific for the chosen cell, the tissue or the host. Preferably, the gene will be an essential gene, so that the organism is only able to replicate in cell, tissue or host, in which the specific promoter functions. In addition to the essential gene, another gene can also be regulated by a promoter or enhancer which is specific for the chosen cell, the tissue or the host.

In the case of the microorganism according to the invention, the specific regulating nucleotide sequence thus functionally replaces a non-specific sequence. In this case, the non-specific regulating sequence is preferably completely or partially removed.

An example of an essential gene for which the promoter can be induced in virtually any cell, in various hosts, is an Immediate Early gene of a virus. The start of the virus infection depends on the expression of such an Immediate Early gene. By replacing the promoter/enhancer of this gene with a promoter/enhancer which is specific for a specific cell, specific tissue or a specific host, the desired specificity is achieved.

The promoter/enhancer which is incorporated in the microorganism to restrict the tropism is chosen depending on the desired and undesired actions of the microorganism. An example of a promoter which can only act in a specific environment is a cytokeratin promoter, such as bovine cytokeratin IV or VIb, which are analogous to, respectively, human cytokeratins 6 and 10 and the vimentin promoter. An example of an inducible promoter is the HSP-70 (heat shock promoter).

Human cytokeratin 6 is expressed in multi-layer epithelium, as present in the mucous membranes of the tongue, in the oesophagus and in the sweat glands of the skin. Human cytokeratin 10 is expressed specifically in keratinocytes of the suprabasal layers of the epidermis. The promoter/enhancer of bovine cytokeratin gene IV is active in epithelial cells of bovine mammary glands which have grown in the presence of hormones but not, for example, in cells of the bovine kidney; this promoter/enhancer is active in mouse keratinocytes but not in mouse fibroblasts.

Vimentin is expressed in cells of mesenchymal origin and in the majority of cells which are kept in tissue culture. Vimentin is not expressed in certain human carcinoma cell lines.

The specific nucleotide sequence which controls the gene of the modified microorganism can be inducible. When the modified microorganism is used to produce immunity, the promoter can thus be induced in the target environment until the desired effect is obtained.

In a particular embodiment of the microorganism according to the invention, the specific nucleotide sequence is a manipulated promoter/enhancer sequence. The activity of the modified microorganism can be further regulated by this means.

The invention also relates to a recombinant virus in which a low-specificity promoter/enhancer of an essential gene has been replaced by a target-specific promoter/enhancer.

The invention also relates to the use of a recombinant microorganism as referred to above for diverse applications in which a cell-specific, tissue-specific or host-specific reaction is desired.

The recombinant microorganism according to the invention can first of all be used to provide protection against the corresponding natural microorganism. This is effected, in particular, in the form of a vaccine. A specific live vaccine of this type has significant advantages because the microorganism, such as a virus with a pathogenic natural strain, is able to replicate only in a tissue, cell or host selected for this purpose and thus is able to generate an immune response in the target organism. The cell, the tissue and/or the host are chosen such that the harmful characteristics of the microorganism, for example the pathogenic characteristics, are not expressed or are expressed only to an acceptable degree, while the immunogenic action is not hindered. An example of this would be the use of a tissue-specific promoter in order to prevent the expression of a specific microorganism in nerve tissue, which is precisely where it displays its pathological action. An advantage of vaccination with a microorganism according to the invention is that, when it replicates under the conditions specific for said microorganism, said micro-organism does not differ from the wild-type organism and therefore can supply all points of attack for an immune reaction. A further advantage arises in the case of the use of a promoter/enhancer which is expressed only in specific species or groups of species. In that case it will be possible to prevent infection from the vaccinated organism to organisms of other species which are sensitive to the wild type. Likewise, by choosing a (tissue- or cell-) specific promoter which is expressed only during a specific development stage of the organism, it is possible to develop a microorganism which is applicable as a vaccine only in that specific stage in the life of the vaccinated organism (for example in young or alternatively in adult animals).

The recombinant microorganism according to the invention can also advantageously be used for combating specific cells. This can be effected, for example, using a cytopathogenic virus. A virus of this type, having a cell tropism which has been modified according to the invention, leaves the organism into which the modified virus has penetrated unharmed with the exception of the cells for which it has been rendered specific. In cells of this type, it is able to exert its cytopathogenic action. In particular, such an application is important for combating cells having a modified expression pattern.

A particular embodiment is the use of a recombinant microorganism according to the invention for combating tumours. In certain tumours combinations of specific proteins, such as, for example, cytokeratins, occur, which combinations are not present in healthy tissue. The recombinant microorganism according to the invention contains promoters which are associated with these proteins. If such promoters control essential genes, the microorganism will replicate only in the tumour cell and generate an immune response against vital and tumour antigens, as a result of which the tumour cell is attacked.

The recombinant microorganism according to the invention can also be used to express a heterologous gene in a desired target environment. A heterologous gene of this type can, for example, code for a medicine or for a product of which a shortage exists in the target environment. In this case, the recombinant microorganism can also contain a target-specific promoter for a replication gene, so that a double specificity arises.

The invention also relates to a vaccine which contains a recombinant microorganism as described above. The invention also relates to medicines and veterinary medicines which contain such a recombinant microorganism.

EXAMPLE I

In this example the replacement of the immediate early gene promoter of the pseudorabies virus (PRV) by a heterologous tissue-specific promoter is described. Reference is made to FIG. 1 for a diagrammatic representation of the method.

FIG. 1. Construction of Tissue Specific Virus

Materials and methods:

The PRV strain NIA-3 (Baskerville, Vet. Bull. 43, 1973, p. 465–480) is multiplied on VN2 cells, a secondary pig kidney cell. SK6 cells, balb/c 3T3 cells and MDBK cells were obtained from ATCC. BMGE+H cells were obtained from Prof. W. Franke, Institut fur Zell-und Tumorbiologie Heidelberg (Heidelberg Institute for Cell and Tumour Biology). The VN2 cells were cultured in EMEM, supplemented with 10% fetal calf serum. SK6 cells, balb/c 3T3 cells and EMGE+H cells were cultured in DMEM, supplemented with 5% fetal calf serum. 1 μg/ml insulin, hydrocortisone and prolactin was added to the medium for the BMGE cells. The MBDK cells were cultured in Eagles Basal, supplemented with 5% fetal calf serum. SK6 cells which produce Immediate Early protein were cultured in DMEM, 5% fetal calf serum and 2.5 mM histidinol.

All DNA recombination operations were carried out in accordance with standard techniques (Maniatis T. et el., Molecular Cloning, A Laboratory Manual, Cold Spring Harbor Laboratory, Cold Spring Harbor N.Y. (1982)). Overlap recombination is described by Van Zyl et el., J. Virology 62, 1988, p. 2191–2195).

The original IE promoter was removed from the subviral fragment C-443 of PRV by treatment of the cosmid C-443 with HindIII. The cleaved DNA was then treated with exonuclease I and then with Mung Bean nuclease, by which means about 600 base pairs were removed at both ends.

A 3 kb XhoI fragment containing the IE promoter therein was cloned in the BamHI site of the pAT-153 vector. The original HindIII site within the pAT vector was removed. The construct obtained was designated pHTXhoIE. Following digestion with BamHI and HindIII, the original IE promoter in this plasmid was then replaced by the promoters of, respectively, bovine cytokeratin IV and VIb (Blessing, M. et el., Differentially expressed bovine cytokeratin genes, EMB0 J. 6, 1987, p. 567–575) and the HSP70 promoter (NAR 8, 1980, p. 3105) (600, 4100 and 450 bp respectively). The plasmids obtained were designated pATXhoCkIV, pATXhocCkVIb and pATXhoHSP. For expression of the Immediate Early protein, the BamHI-8 fragment of PRV, which contains the complete code for the IE, was cloned in the BamHI site of vector pEV.His14.

Recombinant virus was obtained after overlap recombination with the vital subgenome fragments C-179, C-27 and HindIIIB, the fragment C-443 treated as described above and one of the Xho fragments containing the replacement promoter. At the same time, plasmid pEV-IE was added to the transfection mixture. The plaques obtained were examined by means of restriction analysis and hybridisation.

PRV recombinants were thus obtained which express IE under the influence of, respectively, bovine cytokeratin IV, bovine cytokeratin VIb and the HSP promoter. The bovine cytokeratin IV promoter is expressed in bovine mammary gland epithelial cells which are cultured in the presence of hormones but, for example, not in MDBK, SK6 or 3T3 cells. Experiments carried out on cells in tissue culture confirm that the virus mutated with BckIV-PRV displays cell specificity. The virus titres of BckIV-NIA3 mutant virus are 150×higher on BMGE cells than on the other cells. Virus titres of NIA3 are of the same order of magnitude in all cell types. Titration of HSP-NIA3 virus using a temperature cycle of 8 hours at 41.5° C. and 16 hours at 37° C. likewise gives a 150×higher titre than in the case of titration at 37° C.

EXAMPLE II

Animal tests with mice have furthermore demonstrated that both the HSP-NIA3 virus as the BckIV-NIA3 virus are attenuated with regard to the wild type virus (the BckVIb-NIA3 mutant was not included in the animal test). Upon inocculation of 4 to 5 week old balb/c mice with $10^6$ pfu virus in the neck, the average survival time after infection with NIA3 virus is 46 hours (the LD50 for the infection route is 150 pfu). For mice infected with the HSP-NIA3- or the BckIV-NIA3-mutant-virus the average survival time is 65.5 and 82.6 hours respectively. Mutant-virus that could be isolated from the brains of mice demonstrated the same level of inducibility of tissue of specificity as the original mutant-virus-stocks in cell cultures.

These experiments illustrate that it is possible to modify microorganisms, in particular viruses, in a controlled manner with regard to cell tropism and tissue tropism by insertion of specific promoter/enhancer sequences, which may or may not be inducible, for at least one essential gene.

We claim:

1. An immunogenic composition comprising a modified pseudorabies virus (PRV), said modified PRV having a limited tropism in comparison with a corresponding non-modified PRV because in the modified PRV promoter/enhancer sequence of the Immediate Early gene has been replaced by a promoter/enhancer sequence having a different tissue specificity in comparison with that of the native promoter/enhancer sequence of the Immediate Early gene of the non-modified PRV, and a pharmaceutically acceptable carrier.

2. An immunogenic composition according to claim 1, wherein the promoter/enhancer sequence having a different tissue specificity is a promoter/enhancer of a cytokeratin or heat shock protein (HSP).

3. An immunogenic composition according to claim 1, wherein the promoter/enhancer sequence having a different tissue specificity is inducible.

* * * * *

UNITED STATES PATENT AND TRADEMARK OFFICE
CERTIFICATE OF CORRECTION

PATENT NO. : 5,580,564
DATED : December 3, 1996
INVENTOR(S) : Glazenburg et al.

It is certified that error appears in the above-indentified patent and that said Letters Patent is hereby corrected as shown below:

Claim 1, line 5, before "promoter", please insert -- the --.

Signed and Sealed this

Third Day of June, 1997

Attest:

BRUCE LEHMAN

Attesting Officer

Commissioner of Patents and Trademarks